(12) United States Patent
Bruce et al.

(10) Patent No.: US 11,573,434 B2
(45) Date of Patent: Feb. 7, 2023

(54) TUNEABLE OPHTHALMIC LENS

(71) Applicant: CooperVision International Limited, Fareham (GB)

(72) Inventors: Ian Bruce, Southampton (GB); Robert Oag, Southampton (GB)

(73) Assignee: COOPERVISION INTERNATIONAL LIMITED, Fareham (GB)

( * ) Notice: Subject to any disclaimer, the term of this patent is extended or adjusted under 35 U.S.C. 154(b) by 0 days.

(21) Appl. No.: 17/641,447

(22) PCT Filed: Oct. 14, 2020

(86) PCT No.: PCT/GB2020/052578
§ 371 (c)(1),
(2) Date: Mar. 9, 2022

(87) PCT Pub. No.: WO2021/079092
PCT Pub. Date: Apr. 29, 2021

(65) Prior Publication Data
US 2022/0350170 A1    Nov. 3, 2022

(30) Foreign Application Priority Data
Oct. 25, 2019  (GB) .................................. 1915551

(51) Int. Cl.
*G02C 7/08* (2006.01)
*G02C 7/04* (2006.01)
*G02C 11/00* (2006.01)

(52) U.S. Cl.
CPC ............. *G02C 7/085* (2013.01); *G02C 7/041* (2013.01); *G02C 11/10* (2013.01)

(58) Field of Classification Search
CPC ........ G02C 7/085; G02C 7/041; G02C 7/049; G02C 7/08; G02C 11/10; G02B 3/04;
(Continued)

(56) References Cited

U.S. PATENT DOCUMENTS 5,466,260 A * 11/1995 Silvestrini ............... A61F 2/147
606/166
2004/0169932 A1    9/2004 Esch et al.
(Continued)

FOREIGN PATENT DOCUMENTS

WO        01/97742 A2    12/2001
WO     2016173620 A1    11/2016
(Continued)

OTHER PUBLICATIONS

International Search Report and Written Opinion issued in corresponding International Patent Application No. PCT/GB2020/052578 dated Jan. 14, 2021 (11 pages).
(Continued)

*Primary Examiner* — Mustak Choudhury
(74) *Attorney, Agent, or Firm* — Kilyk & Bowersox, P.L.L.C.

(57) ABSTRACT

A tuneable contact lens (100), wherein the contact lens comprises a central region (108). The central region has a circumferential wall and an anterior surface having an external curvature. The contact lens also comprises an inflatable ring (106) arranged around the circumferential wall of the central region, and at least one fluid reservoir (104) in fluid connection with the inflatable ring. The at least one fluid reservoir comprises a pump. When fluid is pumped from the at least one fluid reservoir to the inflatable ring, the inflatable ring inflates and the external curvature of anterior portion of the central region is changed.

18 Claims, 5 Drawing Sheets

(58) Field of Classification Search
CPC ........ G02B 3/06; G02B 3/14; G02B 27/0025; G02B 13/0075; A61F 2/0077; A61F 2/16; A61F 2/1601; A61F 2/1613; A61F 2/1627; A61F 2/1635; A61F 2/1648; A61F 2/1694
See application file for complete search history.

(56) References Cited

U.S. PATENT DOCUMENTS

| | | | | |
|---|---|---|---|---|
| 2011/0085131 | A1* | 4/2011 | Gupta | G02B 27/0025 |
| | | | | 351/159.6 |
| 2011/0118834 | A1 | 5/2011 | Lo et al. | |
| 2018/0217402 | A1* | 8/2018 | Larmagnac | G02B 3/14 |
| 2019/0004325 | A1* | 1/2019 | Connor | G02B 27/0172 |

FOREIGN PATENT DOCUMENTS

| | | |
|---|---|---|
| WO | 2017060537 A2 | 4/2017 |
| WO | 2018125387 A1 | 7/2018 |
| WO | 2019122435 A2 | 6/2019 |

OTHER PUBLICATIONS

International Preliminary Report On Patentability issued in corresponding International Patent Application No. PCT/GB2020/052578 dated Oct. 27, 2021 (with Article 34 claims) (13 pages).

Search and Examination Report issued in corresponding United Kingdom Patent Application No. GB1915551.4 dated Mar. 23, 2020 (6 pages).

Search and Examination Report issued in corresponding United Kingdom Patent Application No. GB1915551.4 dated Jul. 29, 2020 (7 pages).

Examination Report issued in corresponding United Kingdom Patent Application No. GB1915551.4 dated Jan. 25, 2022 (4 pages).

\* cited by examiner

TUNEABLE OPHTHALMIC LENS

This application is a National Stage Application of PCT/GB2020/052578, filed Oct. 14, 2020, which claims priority to United Kingdom Patent Application No. 1915551.4, filed Oct. 25, 2019, which are incorporated in their entirety by reference herein.

FIELD OF THE PRESENT DISCLOSURE

The present disclosure concerns ophthalmic lenses. More particularly, but not exclusively, this present disclosure concerns tuneable contact lenses.

BACKGROUND OF THE INVENTION

A significant number of people suffer from vision defects, for example myopia (short sightedness) or hyperopia (long sightedness). As people get older, they develop presbyopia (where the lens becomes less elastic which makes it more difficult for the eye to accommodate, i.e. to increase its focusing power to focus on near objects). A common way of correcting the vision in this situation is the use of varifocal eyeglasses. These glasses have a different focal length near the top of the lens compared with the bottom of the lens; however, this means that vision through part of the lens is always out of focus depending on the activity of the wearer, and as such many people opt for two separate pairs of glasses: one for near sight and one for far sight. This is cumbersome and impractical.

Conventional ophthalmic lenses are set at a specific power that is determined when the ophthalmic lens is manufactured, and as such are unable to remedy the above issue by themselves. Some alterative conventional ophthalmic lenses have been designed to overcome this problem. One way is for each contact lens of a contact lens pair to have a different optical power. For example, the contact lens in the left eye might have a power for distance vision, and the contact lens in the right eye might have a power for near vision. This is termed 'monovision' as the wearer of this type of contact lens system no longer has binocular vision, which is a problem. Another alternative design is to have a contact lens with a central optical zone that encompasses parts of the contact lens with different powers. For example, the centre of the central optical zone might have a power for near vision, and a ring shaped region around the centre (still within the central optical zone) may have a power for distance vision. This produces two images on the retina, and the neural optical pathways of the wearer are required to select which image to 'look' at. Some variants of this have more than one zone of each power. Many wearers complain of problems including ghosting when using contact lenses of this variety. It would therefore be desirable to have an ophthalmic lens that is capable of adjusting its power, not only for near and far sight, but also for when the strength of correction required by the eye changes with time.

Ophthalmic lenses have been proposed that have a central region that is inflatable with fluid. WO 2019/122435 discloses a contact lens with a lens volume that is supplied with fluid from adjacent fluid reservoirs. As the lens volume is filled with fluid, it changes shape and therefore changes its focal length/power. One of the problems associated with the prior art is that if there is a loss of power, then the power of the lens is also lost, and can leave the wearer with blurred vision.

The present disclosure seeks to mitigate the above-mentioned problems. Alternatively or additionally, the present invention seeks to provide an improved tuneable ophthalmic lens.

SUMMARY OF THE PRESENT DISCLOSURE

The present disclosure provides, according to a first aspect, a tuneable contact lens as claimed in claim 1.

According to a second aspect of the present disclosure, there is also provided a method of tuning a contact lens as claimed in claim 13.

According to a third aspect of the present disclosure, there is also provided a method of manufacturing a tuneable contact lens as claimed in claim 14.

According to a fourth aspect of the present disclosure, there is also provided a kit of parts as claimed in claim 17.

Optional but preferred features are set out in the dependent claims.

It will of course be appreciated that features described in relation to one aspect of the present invention may be incorporated into other aspects of the present invention. For example, the method of the invention may incorporate any of the features described with reference to the apparatus of the invention and vice versa.

DESCRIPTION OF THE DRAWINGS

Embodiments of the present disclosure will now be described by way of example only with reference to the accompanying schematic drawings of which.

DETAILED DESCRIPTION

Figure 1:
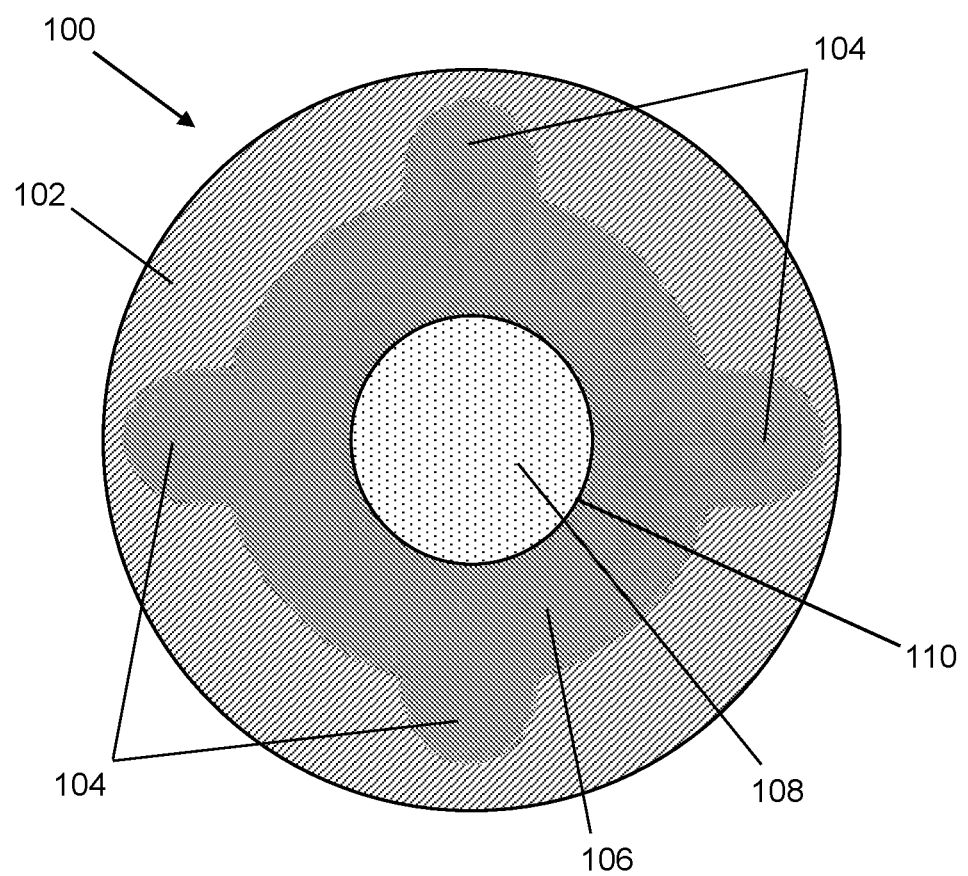
FIG. 1 shows a front view of an ophthalmic lens according to an embodiment of the present disclosure.

The present disclosure will be more fully understood and further advantages will become apparent when reference is made to the following detailed description of embodiments of the present disclosure, wherein like reference numeral denote similar elements. (Note that the figures are not to scale.)

In the following description, the terms "first lens portion" and "second lens portion" refer to portions that form part of an ophthalmic lens. Optionally, first lens portion is not a lens, i.e. the power of first lens portion may be substantially zero. Optionally, second lens portion is not a lens, i.e. the power of second lens portion may be substantially zero. When specifically in reference to contact lenses, the first lens portion refers to the portion that makes up the contact lens that is in contact with an eyeball when the contact lens is in use. The second lens portion, when in reference to contact lenses, refers to the portion, which makes up the contact lens, which is not in contact with the eyeball and which forms part of the external curvature of the contact lens, when the contact lens is in use on an eye.

The term "central optical zone" refers to the region of the ophthalmic lens that is configured to be positioned over the pupil of an eye when in use. The central optical zone may encompass a portion of the central region. The central optical zone may encompass the entirety of the central region. The central optical zone may encompass the entirety of the central region, and a section of the second lens portion. The central optical zone may encompass the entirety of the central region, and a section of an annular ring. The central optical zone may encompass the entirety of the central region and the entirety of the annular ring.

As set out above, the first aspect of the present disclosure provides according to a first aspect a tuneable ophthalmic lens. The tuneable ophthalmic lens comprises a central region. The central region has (i) a circumferential wall and (ii) an anterior surface having an external curvature. The tuneable ophthalmic lens also comprises an inflatable ring. The inflatable ring is arranged around the circumferential wall of the central region. The inflatable ring is an annular ring. The tuneable ophthalmic lens also comprises at least one fluid reservoir in fluid connection with the inflatable ring. The tuneable ophthalmic lens further comprises a pumping mechanism. The pumping mechanism is a pump. The pump is arranged to pump fluid from the at least one fluid reservoir to the inflatable ring. When fluid is pumped from the at least one fluid reservoir to the inflatable ring, the inflatable ring is inflated and the external curvature of the anterior surface of the central region is changed. The external curvature of the central optical zone may be changed.

The inflatable ring may share in common with the central region the circumferential wall and the thickness (in the direction at right angles to the surface of the eye) of the central region at its circumference may increase as the inflatable ring inflates. The anterior surface of the central region may extend over at least a portion of an upper surface of the annular ring. As the inflatable ring inflates, its upper surface may rise relative to the rest of the lens. In embodiments, the increase in height of the inflatable ring raises the height of the shared circumferential wall in common with the central region. This, in turn, may increase the thickness of the central region at its circumferential region. The increased thickness of the central region at its circumference may cause the external curvature of the central region to become more flat. The increased thickness of the central region at its circumference may cause the external curvature of the anterior surface of the central region to become reduced. The reduction in curvature of the external curvature of the anterior surface of the central region may cause the central region to reduce its optical power. In embodiments, the increase in height of the inflatable ring raises the height of an extended anterior surface of the central region. This, in turn, may increase the thickness of the central region at its circumferential region. The increased thickness of the central region at its circumference may cause the external curvature of the anterior surface of the central region to become more flat. The increased thickness of the central region at its circumference may cause the external curvature of the anterior surface of the central region to become reduced. The reduction in curvature of the external curvature of the anterior surface of the central region may cause the central region to reduce its optical power.

The boundary of the central region is partly defined by a circumferential wall and an anterior surface having an external curvature. The boundary of the central region may be defined by a surface of a first lens portion. The central region may comprise a void between the first lens portion and a second lens portion.

The central region may be filled with fluid to a predetermined volume. The filling of the central region to a predetermined volume may occur when the ophthalmic lens is manufactured. The volume of fluid in the central region may remain unchanged when the ophthalmic lens is in use. The inflatable ring may be in a deflated state when the ophthalmic lens is manufactured. This advantageously means that should the ophthalmic lens ever lose electrical power, the ophthalmic lens would revert to the power that was set when the lens was manufactured. The central region may be entirely solid. The central region may comprise a hydrogel, a silicone hydrogel, or a silicone elastomer. Optionally, there is no cavity in the central region, and the central region may be a hydrogel, a silicone hydrogel, or a silicone elastomer. The solid central region may be deformable (for example, such that the external curvature of the anterior surface may be adjusted by inflation of the inflatable ring). The central region may comprise a solid portion and a fluid filled portion. The fluid filled portion may be a liquid filled portion. The inflatable ring may be positioned to be adjacent to substantially the entire circumferential wall of the central region. The inflatable ring may be connected to substantially the entire circumferential wall of the central region. The connection between the inflatable ring and the circumferential wall of the central region may be such that a change in shape of the inflatable ring changes the shape of the central region in an area proximal to the circumferential wall. ("Substantially the entire circumferential wall of the central region" may refer to at least 80%, or at least 90%, or at least 95%, or at least 97%, or at least 99% of the circumferential wall of the central region.) This advantageously means that when the inflatable ring is inflated with fluid, the external curvature of that anterior surface of the central region is uniformly changed across its surface. The anterior surface of the central optical zone may be uniformly changed across its surface. As the inflatable ring is inflated, the region of the central region that is closest to its circumference is raised and the net curvature of the central region is reduced. The net curvature of the central optical zone may be reduced. This reduction in the net curvature of the central region makes the lens less convex or more concave, reducing the optical power of the lens (i.e. makes the power of the lens move towards the negative direction). As the inflatable ring is deflated, the net curvature of the central region increases. This would make the lens more convex or less concave, increasing the optical power of the lens. The amount of fluid in the inflatable ring may be continuously adjustable, and therefore the curvature of the central region may be continuously adjusted to suit any circumstances and requirements.

The internal circumference of the inflatable ring of the tuneable ophthalmic lens of the first aspect may share a portion of the lens with the circumferential wall of the central region. The internal circumference of the inflatable ring may be connected to portions of the circumferential wall of the central region. The internal circumferential wall of the inflatable ring may be connected to portions of the circumferential wall of the central region via the portion of the lens. The connection to the central region may be continuously around the circumferential wall such that the curvature adjustment of the central region is uniform.

The external circumference of the inflatable ring of the tuneable contact lens of the first aspect may be positioned to be adjacent to the circumferential wall of the central region. In embodiments of the present disclosure, the inflatable ring may be located inside the central region. Similar advantages of having the inflatable ring located inside the central region are obtained compared to having the inflatable ring outside the central region (i.e. the internal circumference of the inflatable ring, rather than the external circumference being positioned to be adjacent to the circumferential wall of the central region).

The central region may be configured to be positioned over the pupil of an eye when in use. The ophthalmic lens may be a contact lens. The ophthalmic lens may be an intraocular lens. In such embodiments, the shape of the contact lens would not need to be matched to the external curvature of the eye. The advantages of having a tuneable contact lens of the first aspect for positioning on the surface of the eye (contact lens) are similar to the advantages of having a tuneable contact lens for positioning inside the eye (intraocular lens).

The pumping mechanism may include a wireless communication module. The wireless communication module may receive instructions. The instructions may control the pumping mechanism. The wireless communication module may be configured to communicate with a control unit. The control unit may be external to the ophthalmic lens. The control unit may transmit instructions to the wireless communication module. The control unit may receive manual inputs from a wearer of the ophthalmic lens. The control unit may convert manual inputs into instructions, which are then transmitted to the wireless communication module. The control module may convert the manual inputs into a setting. The setting may be transmitted to the pump. The volume of fluid pumped by the pump may be a function of the setting. The communication between the control unit and the wireless communication module may be radio frequency.

The wearer may for example input to the control unit that they wish to see long distance. The control unit may be calibrated for the wearer, such that the wearer input is converted into an appropriate instruction for the pumping mechanism. The curvature of the central region is then adjusted such that the wearer can see clearly in long distance. The wearer may then input into the control unit that they wish to see short distance, for example. The control unit would then convert the wearer's input into an appropriate instruction for the pumping mechanism. The curvature of the central region would then be adjusted such that the wearer can see in short distance.

The pumping mechanism may be an osmotic pump. An osmotic pump does not require high voltages to operate, and so advantageously means that the ophthalmic lens will be operable for longer periods of time before a recharge is required. Osmotic pumps are also beneficial in that they are capable of accurately and precisely moving specific quantities of fluid across its osmotic membrane. The pumping mechanism may be an actuator or may be a mechanical pump.

When the inflatable ring is deflated, the central optical zone may be considered to be in its strongest power. The strongest power may be configured to assist the wearer of the lens in viewing objects in the near vision. As the inflatable ring is inflated, the net curvature of the central region decreases and the power of the lens moves towards the negative direction (this encompasses large positive powers reducing to smaller positive powers, positive powers becoming negative powers, and negative powers becoming more negative powers). The largest reduction in power from the strongest power of the lens, by inflating the inflatable ring, may be for example four dioptres. For example, when the inflatable ring is deflated, the power of the lens may be +1.25 dioptres, and when the inflatable ring is fully inflated the power of the lens may be −2.75 dioptres. The difference in the power of the lens, may be at least one dioptre, or may be at least two dioptres, or may be at least three dioptres, between when the inflatable ring is fully deflated to a fully inflated state.

When the inflatable ring is deflated, the inflatable ring may be substantially empty of fluid. Substantially empty may correspond to a volume of fluid less than or equal to 5%, or 4%, or 3%, or 2%, or 1% of the maximum capacity of the inflatable ring. The volume of fluid left in the inflatable ring when the inflatable ring is deflated may be the amount of fluid that inherently remains when the pumping mechanism is inactive. The pumping mechanism may be inactive because it has been instructed to return the ophthalmic lens to its strongest power, or it may be receiving no power due to the ophthalmic lens running out of electrical power. The reason that fluid may remain in the inflatable ring when the inflatable ring is deflated may be an inherent result of the shape of the inflatable ring. Optionally, the inflatable ring does not lie completely flat, when deflated, as a result of its connection to the central region. Fluid may remain along the edges of the inflatable ring that do not lie completely flat when deflated.

The external curvature of the central region may be greatest when the inflatable ring is deflated, i.e. when the inflatable ring is deflated, the lens may be at its maximum power. The external curvature of the central region may be at its minimum when the inflatable ring is full, i.e. when the inflatable ring is full, the lens may be at its minimum power.

It may be that the circumferential wall does not extend in a substantially perpendicular direction to the surface of an eye, when the ophthalmic lens is in use. The circumferential wall may be angled towards the centre of the central region. The inflatable ring may overlap a portion of the circumferential wall, when the ophthalmic lens is viewed in plan view. The overlapping portion may be a portion of the circumferential wall that is angled towards the centre of the central region. The inflatable ring may overlap the entire anterior surface of the central region. The overlapping portion may enable a smoother external curvature of the central optical zone to be achieved. It may be that the central optical zone encompasses only a portion of the overlapping portion. The overlapping portion may include a step. The step may have a thinner step at the periphery of the central region, and a thicker step closer to the centre of the central region.

The central region may be circular in plan view. The central region may be an oval in plan view. The inflatable ring may be complementary in shape to the central region. Therefore, for example, if the central region is oval, the inflatable ring may also be an oval in its interior and exterior circumferential boundary. The internal circumference of the inflatable ring may be the same shape as the circumferential wall of the central region. The skilled person will know that the term "circumference" is not limited to circles, and also includes the perimeter of ovals/ellipses. The central region may be elliptical in plan view. The internal circumference of the inflatable ring may be elliptical in plan view. Optionally, the cross section of the inflatable ring through a vertical plane (in the on-eye orientation) may be non-uniform. This may enhance correction of coma due to gravity. The correction may be achieved by the inflatable ring being able to contain more fluid at the top of the ring compared to at the bottom of the ring. The inflatable ring may be larger at the top than at the bottom.

The central region may be smaller than the inflatable ring. The central region may have a radius less than the width of the inflatable ring. The width of the inflatable ring is the difference between its external radius and its internal radius. Difference may be an average of the difference between the external radius and the internal radius. The average may be a mean average. The radius of the central region may be less than 80% of the width of the inflatable ring. The radius of the central region may be less than 60%, or 50%, or 40%, or 30%, or 20%, or 10% of the width of the inflatable ring. The central region may comprise a pillar structure in the centre of the central optical zone. The pillar structure may be configured to support the inflatable ring. Having a relatively small radius of the central region may result in a smoother external curvature of the ophthalmic lens.

The inflatable ring may be either a plurality (at least three, for example) of inflatable portions arranged around the central region to form a ring. Each of plurality of the inflatable portions may be positioned to be adjacent to a portion of the circumferential wall of the central region.

The tuneable ophthalmic lens of the first aspect may comprise a sensor. The sensor may be configured to detect whether a wearer of the lens is looking in long distance or short distance. The sensor may comprise a range finder. The range finder may be configured to determine a distance of an object. The distance of the object may be the distance of the object, which a wearer of the lens is observing, from the lens. The sensor may communicate information to a control module. The control module may be comprised in the lens. The control module may convert the information into a setting. The setting may be transmitted to the pump. The volume of fluid pumped by the pump may be a function of the setting.

As set out above the second aspect of this disclosure provides a method of tuning an ophthalmic lens. The ophthalmic lens comprises a central region having (i) a circumferential wall and (2) an anterior surface having an external curvature. The ophthalmic lens also comprises an inflatable ring, which is arranged around the circumferential wall of the central region. The ophthalmic lens further comprises a fluid reservoir, and a pumping mechanism. The pumping mechanism is a pump. The method comprises the step of activating the pumping mechanism to pump fluid from the fluid reservoir to the inflatable ring. This inflates the inflatable ring and thereby changes the external curvature of the anterior surface of the central region.

As set out above the third aspect of the present disclosure provides a method of manufacturing a tuneable ophthalmic lens according to the first aspect. A first lens portion is formed. A second lens portion is formed. A first and second recess are formed in the first and/or second lens portions. A fluid reservoir is formed in the first and/or second lens portion. A pump is positioned to be in fluid communication with the fluid reservoir. The method further comprises bonding the second lens portion to the first lens portion. The bonding is such that the first recess forms a central region. The bonding is also such that the second recess forms an inflatable ring.

The ophthalmic lens may be a contact lens.

The method of manufacturing according to the third aspect may comprise forming a first and second mold part. The method may comprise filling a gap between the first and second mold part with first lens portion material. The method may further comprise curing the first lens portion material.

Forming the first and second recess may comprise plastically deforming the second lens portion. This may be achieved by holding the second lens portion in place while a recess forming arm is pressed into the second lens portion. This may be done multiple times, with recess arms of different diameters to form different sized recesses in the second lens portion.

The skilled person will appreciate that the order of the steps as set out in the method of the third aspect are not limited to the order presented. For example, it would be possible to form the second lens portion before forming the first lens portion.

As set out above the fourth aspect of the present disclosure provides a kit of parts comprising: (a) a tuneable ophthalmic lens as claimed in any of claims 1 to 12, the lens including a communication module; and (b) a control module for communicating with the communication module.

FIG. 1 shows a front view of a tuneable contact lens 100 according to an embodiment of the present disclosure. The majority of contact lens 100 is comprised of first lens portion 102. First lens portion 102 is shaped to fit on the eye, and has a concave rear surface. First lens portion 102 is constructed out of silicone elastomer, which is beneficial in contact lenses for its oxygen and water permeability, and for preventing the eye from drying out.

In the centre of lens 100 is a central region 108. Central region 108 is a sealed region filled with fluid. Central region 108 is circular in shape. The fluid is a liquid with a chosen refractive index. The walls of central region 108 are flexible, and is deformable under external force/pressure. When under substantially no external force/pressure (excluding gravity), central region 108 is in its default shape.

Contact lens 100 also comprises an inflatable ring 106 arranged around central region 108. Inflatable ring 106 is an annular ring 106. Annular ring 106 is connected to circumferential wall 110 of central region 108. Annular ring 106 is inflatable with fluid. The fluid used to inflate/deflate annular ring 106 is supplied from fluid reservoirs 104, which are in fluid connection with annular ring 106. Annular ring 106 is not in fluid connection with central region 108, and is only in physical connection with central region 108. There are four fluid reservoirs 104. In embodiments of the invention, there may be fewer than four fluid reservoirs 104. There may be one, or two, or three fluid reservoirs for example. In embodiments of the invention, there may be more than four fluid reservoirs. There may be any number of fluid reservoirs between four and ten, and even up to twelve, for example.

Fluid reservoirs 104 comprise pumping mechanisms (not shown). The pumping mechanism is a pump. The pump is an osmotic pump. The pump includes a wireless communication module. The wireless communication module communicates wirelessly to a control unit (not shown) external to the contact lens. The wearer of the contact lens is able to input commands into the control unit which instructs the pump how much fluid to pump into/remove from annular ring 106.

Figure 2A:
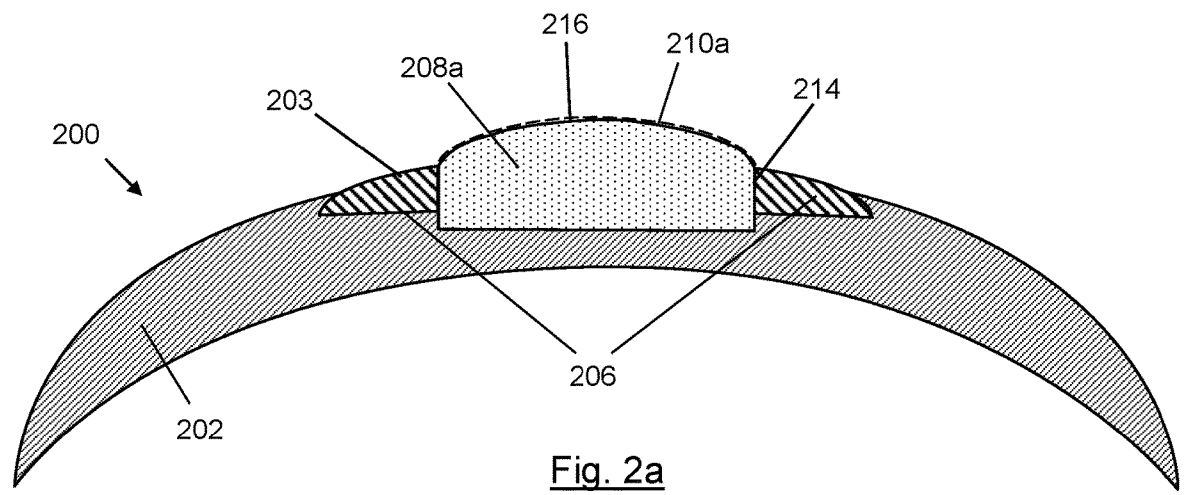
FIG. 2a shows a cross-sectional side view of an ophthalmic lens in a deactivated state according to an embodiment of the present disclosure.
Figure 2B:
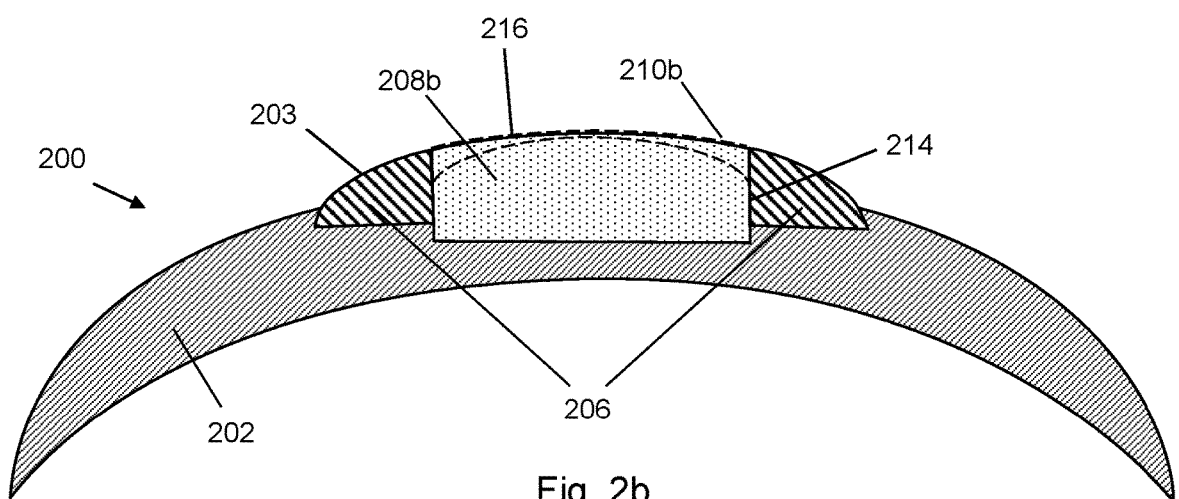
FIG. 2b shows a cross-sectional side view of an ophthalmic lens in an activated state according to an embodiment of the present disclosure.

FIGS. 2*a* and 2*b* show cross-sectional side views of contact lens 200 in a deactivated state and an activated state respectively. The deactivated state may refer to a deflated state, wherein the deflated state is defined by annular ring 206 being substantially empty of fluid. Substantially empty of fluid refers to when annular ring 206 contains a volume of fluid equivalent to 5% or less of its maximum capacity. The activated state may refer to an inflated state, wherein the inflated state is defined by annular ring 206 being at least partially inflated. At least partially inflated refers to when annular ring 206*b* contains a volume of fluid equivalent to greater than 5% of its maximum capacity. (The external curvatures 210*a*, 210*b*, 260 in FIG. 2 are exaggerated and not representative of curvatures that would be achieved when physically using the contact lens 200, 250. The skilled person will appreciate that the exaggeration of the external curvatures 210a, 210b, 260 is to more clearly show a difference in curvature between an activated and deactivated state of the contact lens 200 250, for purposes of illustration.)

FIG. 2a shows contact lens 200 in the deactivated state. Central region 208 at second lens portion 203 is at its maximum power, which refers to the power of central region 208 that is set when contact lens 200 is manufactured. Annular ring 206 is substantially empty of fluid, and therefore has no effect on external curvature 210a of anterior surface 216 of central region 208a.

FIG. 2b shows contact lens 200 in the activated state. Fluid reservoirs (not shown), which are similar to the fluid reservoirs 104 of FIG. 1, have pumped fluid into annular ring 206. Because the internal circumference of annular ring 206 is connected to circumferential wall 214 of central region 208, as annular ring 206 is inflated with fluid, this pulls the upper surface of central region 208 in the region near its circumference moves away from first lens portion 202, and thereby increases the thickness of central region 208 at its circumference. As the volume of fluid in central region 208 is fixed, external curvature 210b is less than external curvature 210a of anterior surface 216. The more inflated annular ring 206 becomes, the lower the external curvature 210b of anterior surface 216 of central region 208 becomes. The lower external curvature 210b results in the power, of contact lens 200, heading in the negative direction. In the example, the difference in power of contact lens 200, between annular ring 206 being fully deflated and fully inflated, is four dioptres, i.e. the power of contact lens 200 when annular ring 206 is fully inflated is four dioptres lower than the power of contact lens 200 when annular ring 206 is fully deflated.

Figure 2C:
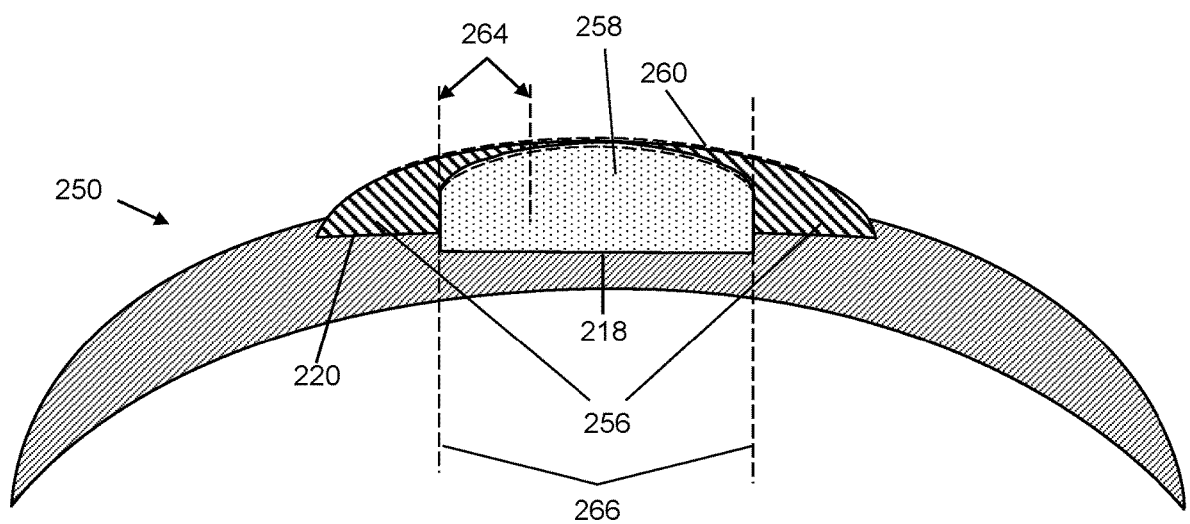
FIG. 2c shows a cross-sectional side view of an ophthalmic lens in an activated state according to another embodiment of the present disclosure.

FIG. 2c shows a contact lens 250 in the activated state, according to an embodiment of the present disclosure. An inflatable ring 256 overlaps a central region 258 in an overlapping portion 264. The overlapping portion 264 is ring shaped, and concentric with the inflatable ring 256. When the contact lens 250 is deactivated, fluid is pumped out of the inflatable ring 256, and there will subsequently be substantially no fluid in the portion of the inflatable ring 256 that occupies the overlapping portion 264. The central optical zone 266 encompasses the central region 258 and the overlapping portion 264. The use of an overlapping portion enables the external curvature 260, including the curvature of the central region 258, to be smooth. This is because the thinner sections of the overlapping portion of the inflatable ring 256 inflates to a lesser volume than the thicker sections. Thus, the tapered shape of the inflatable ring 256 causes the curvature of the central region 258, and the central optical zone 266 to be smooth.

Figure 3:
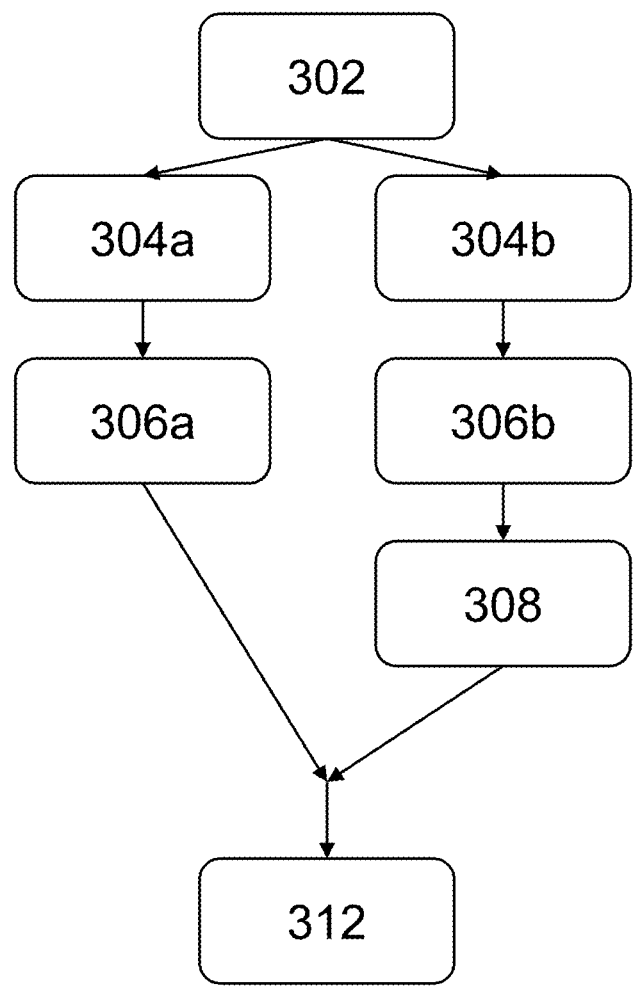
FIG. 3 shows a flow chart of a method of manufacturing an ophthalmic lens according to an embodiment of the present disclosure.

The following is an exemplary method of manufacture of a contact lens, according to an embodiment of the present disclosure. FIG. 3 shows a flowchart of a method of manufacturing an ophthalmic lens according to an embodiment of the present disclosure.

The method comprises the step of forming a first lens portion. The first lens portion is formed of silicone hydrogel or silicone elastomer. The first lens portion is formed in a lens portion molding assembly, which comprises a first mold part and a second mold part assembled together. The first and second mold parts are formed in mold part forming step 302. Mold part forming 302 uses metal dies. A surface of each of a pair of metal dies corresponds to a surface of a mold part to be formed. Considering that only one surface of the mold part to be formed is used in the formation of any of the contact lens components, the die used to form the other surface does not need to form a particular shape. One of the dies may be flat, for example. The other die may have a concave cavity. This forms a mold part with a convex anterior surface and a flat rear surface. Mold part forming 302 includes holding the dies together and injection molding a first mold part. A similar second pair of dies are used to form a second mold part, also by injection molding. The second pair of dies may include a die with a convex protrusion, while the second die of the second pair may be flat. The mold part formed in this second pair of dies would therefore have a concave surface and a flat (rear) surface.

Mold part forming step 302 also includes the formation of a pair of injection molded molds that are used to form a second lens portion. The steps for forming the pair of molds for forming the second lens portion are substantially the same as the steps for forming the pair of molds for forming the first lens portion. The injection molded molds for forming the second lens portion may be a different shape to the molds for forming the first lens portion.

In this example, the die forming the concave surface includes recesses that lead to the formation of recesses in the second lens portion, the recesses corresponding to the central region, the inflatable ring, the fluid reservoir and channels therebetween. FIG. 2c illustrates first recess 218 and second recess 220.

A dry first lens portion is then formed in first lens portion forming step 304a. A dry second lens portion is also then formed in step 304b. The steps for the formation of both of these lens portions is substantially the same and is as follows. In the case of hydrogel members or silicone hydrogel members, the first lens portion (or second lens portion) can be made by polymerizing a hydrogel or silicone hydrogel lens formulation that includes a polymerization initiator in a first lens portion shaped cavity formed between the first mold part and the second mold part. For silicone elastomer members, the first lens portion can be made by curing, vulcanizing, or catalyzing, such as by hydrosylation, a liquid silicone elastomer material in a first lens portion shaped cavity formed between the first mold part and the second mold part. The surface of each mold part that forms the lens member shaped cavity may be convex, concave, planar or a combination of thereof. After formation of the first lens portion, the two mold parts are separated such that the first lens portion remains attached to the surface of one of the mold parts. As a result, a first lens portion is provided on a surface of the first or second mold part. In embodiments of the present disclosure, it is desirable to place the first lens portion on a surface of a mold part that was not used to produce the first lens portion, but that may require additional steps to achieve the desired alignment of the member to the mold part.

Washing steps 306a and 306b involve washing of the first lens portion and the second lens portion respectively. Any residue from the formation of the first lens portion and the second lens portion in the mold parts is washed off. Also in this step, the washing causes the dry lens parts to swell as water may be retained within the membrane of the lens parts.

In a recess enhancing step 308, the second lens portion is held in a receptacle. A recess enhancing surface of a predetermined diameter is then pressed into the concave surface of the second lens portion to plastically deform the recess in the second lens portion that will go on to form the central region. The second lens portion is plastically deformed in the region of the central region so that the portion of the upper layer that forms the walls of the central region are not under stress when the central region is filled with fluid, when in use. It has been found that without plastically deforming the walls of the central region, when the central region is filled with fluid, the stress in the walls of the central region caused by the elasticity of the walls of the central region exert excessive pressure on the fluid contained within the central region. This pressure exerted by the walls of the central region on the fluid contained therein can cause fluid to either leak out of the central region, and/or back into a fluid reservoir, which is undesirable. A second recess forming arm of a different diameter to the first is then pressed incident on the concave side of the second lens portion to further, plastically, deform a second portion of the second lens portion outwards. The second recess forming arm may be ring shaped, or the second recess forming arm may comprise at least three smaller recess forming protrusions. The second set of deformations made to the second lens portion forms the annular ring. Therefore, the second set of recesses is arranged such that it/they are formed around the first recess (which forms the central region). A third recess may be formed by a third recess forming arm, to form a fluid reservoir. A pumping mechanism may be positioned to be in fluid communication with the fluid reservoir, when in use. The pumping mechanism is a pump. The fluid reservoir and the annular ring may be formed in one formation step, as opposed to two separate formation steps followed by a connections step. Optionally, the central region may be formed in first lens portion forming step 304a. Optionally, the central region may be formed in both first lens portion forming step 304a and second lens portion forming step 304b. The recess that forms the central region may be cast molded into either, or both, of the first and second lens portions in their respective forming steps 304a, 304b.

The method further comprises bonding step 312. Bonding step 312 is the step of bonding the first lens portion to the second lens portion, to form a tuneable contact lens. As mentioned earlier in the description, the "second lens portion" includes the central region, annular ring, and fluid reservoir.

The first lens portion or second lens portion is provided on a compliant stage. The compliant stage may have a greater flexibility than the first and/or second mold parts. The provision of the first lens portion or the second lens portion on the compliant stage can be done manually, or it can be done using an automated machine, such as a robotic device. Optionally, each of the first lens portion and/or second lens portion is provided on a compliant stage.

The compliant stage provided as a support for the first lens portion and/or second lens portion may be of a material that is more pliable than the material of the first mold part and/or second mold part. Using a deformable material to form the compliant stage facilitates ensuring proper alignment and sufficient bonding of the second lens portion to the first lens portion. For example, the contact between the second lens portion and the first lens portion is more complete than when the first lens portion is provided on a rigid convex surface.

The second lens portion is provided on a concave surface. Fluid is then dispensed into the concave side of the second lens portion such that it sits within the recesses formed in recess step 308. Fluid is dispensed into the first deformed portion such that it is filled. This is the central region, and its shape in this stage determines what the strongest power of the eventual contact lens will be. Fluid is also dispensed into the fluid reservoir, but not the annular ring. This is to ensure that when the contact lens is eventually formed, it is known to be possible to evacuate all of the fluid from the annular ring. Optionally, fluid is dispensed into the annular ring and not the fluid reservoir. Fluid may be dispensed into both the annular ring and the fluid reservoir such that they are both partially filled with fluid.

The first lens portion located on the compliant stage is placed in contact with the second lens portion. The placement of the first lens portion on the second lens portion is such that the second lens portion is aligned with the first lens portion, and the compliant stage/stages provides compression to the second lens portion and/or first lens portion.

Once the second lens portion and the first lens portion are in contact, the methods of the present disclosure then include a step of bonding the second lens portion and the first lens portion to form the tuneable contact lens. The bonding can be achieved using an adhesive, or curing the components together, and the like. This bonding step of the method may include one or more of the following steps:

Modifying a surface of the first lens portion and or second lens portion, for example prior to bringing the first lens portion and second lens portion into contact;

Bonding the second lens portion to the first lens portion, for example by heating the second lens portion and the first lens portion while they are in contact;

Clamping the second lens portion and the first lens portion while they are in contact, for example before bonding;

According to embodiments of the present disclosure, the methods include a step of modifying a surface, e.g. a concave surface, of the second lens portion and/or modifying a surface, e.g. a convex surface, of the first lens portion by exposing the second lens portion and/or the first lens portion respectively to a plasma treatment process. In other words, the surfaces of the second lens portion and first lens portion can be activated by exposing them to plasma.

Figure 4:
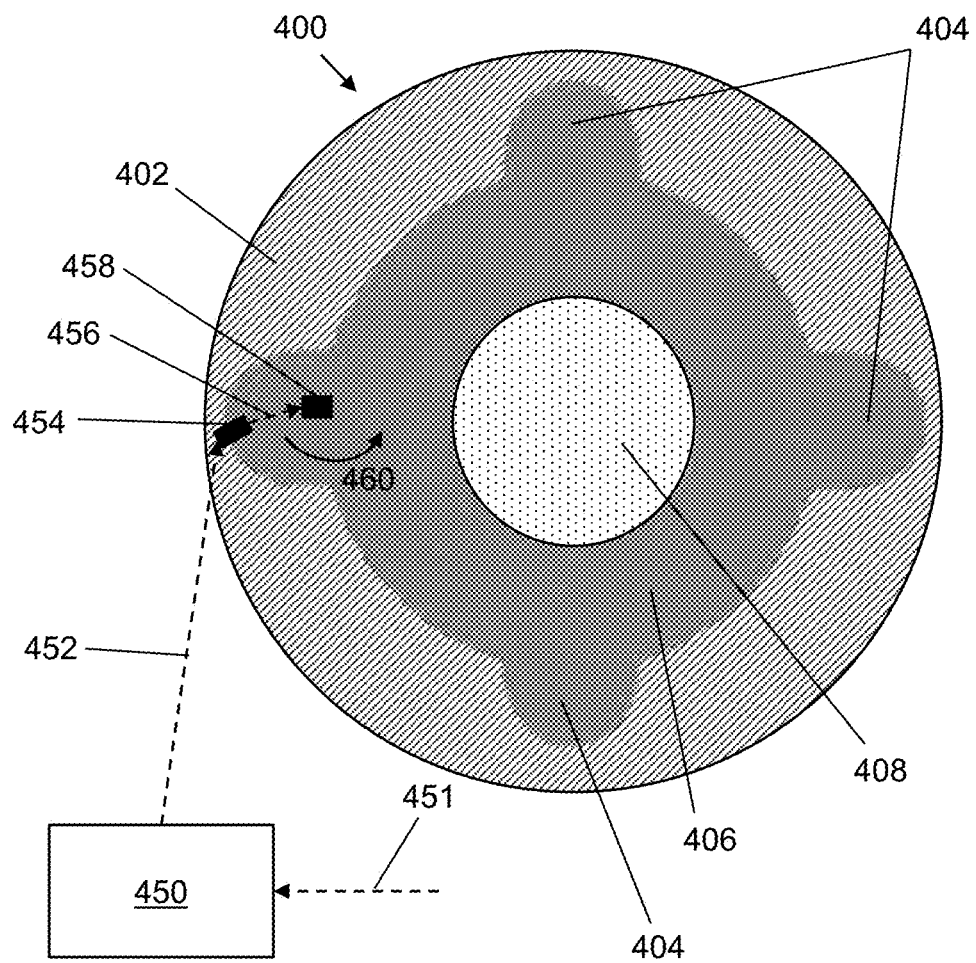
FIG. 4 shows a schematic diagram of a method of tuning an ophthalmic lens according to an embodiment of the present disclosure.

In the embodiment of FIG. 4, the ophthalmic lens is a contact lens. Contact lens 400 is similar in structure to contact lens 100 of FIG. 1. Central region 408 is filled with fluid. Contact lens 400 comprises a pump 458. Pump 458 is located within a fluid reservoir 404.

The pump may be located adjacent the respective fluid reservoir. In such embodiments, the pump may apply external pressure to the fluid reservoir to increase the internal pressure within the fluid reservoir, and therefore force fluid out of the fluid reservoir and into the central region. The pump may be located at an outlet of the fluid reservoir. The pumping mechanism may be located at an entrance to the central region. The outlet of the fluid reservoir may be in direct fluid communication with the central region. The pump may be located within a fluid channel. The fluid channel may be configured to allow fluid communication between the fluid reservoir and the central region.

Pump 458 includes a wireless communication module 454. Wireless communication module 454 communicates pump settings 456 to pump 458. There is also provided a control module 450. Control module 450 communicates wirelessly to wireless communication module 454. Control module 450 is configured to receive manual inputs 451 from a wearer of contact lens 400. Control module 450 is external to contact lens 400.

Control module 450 may be comprised in a mobile telephone device. The interface by which a wearer of the ophthalmic lens may provide manual inputs may be a software application on a device. Control module 450 may be comprised in a bespoke device designed to house a control module for tuning an ophthalmic lens.

Control module 450 receives manual inputs 451 from the wearer of contact lens 400, and converts the inputs 451 into an instruction 452. Control module 450 communicates instruction 452 to wireless communication module 454. The instruction comprises an indication of the volume of fluid to be present in annular ring 406. The indication may be that annular ring 406 is required to be completely filled with fluid. The indication may be that annular ring 408 is required to contain substantially no fluid.

The instruction may comprise switching the pump on. The instruction may comprise switching the pump off. The instruction may comprise an "on" instruction, and an "off" instruction. In embodiments where there is a second pump (not shown) in another fluid reservoir 404, the same instructions and settings may be communicated to each pump. For example, first wireless communication module 454 of first pump 458 may receive an instruction comprising an "off" instruction, and a second wireless communication module of a second pump (provided in a second fluid reservoir 404) may also receive an instruction comprising an "off" instruction. For example, first wireless communication module 454 of first pump 458 may receive an instruction comprising filling central region 408 25% full of fluid, and a second wireless communication module of a second pump (provided in second fluid reservoir 404) may also receive an instruction comprising filling central region 408 25% full of fluid.

Wireless communication module 454 converts instruction 452 to pump setting 456. In the embodiment of FIG. 4, pump setting 456 comprises switching pump 458 "on", such that pump 458 pumps fluid into central region 408, and such that central region 408 is full of fluid.

The control module may comprise a plurality of predetermined instructions. The instructions may be pre-calibrated for the prescription of the wearer of the contact lens. The user input may comprise requesting that the contact lens switch between near vision, and distance vision. There may be other distances that the contact lens is configured to switch between. The user input may comprise requesting that the contact lens switch to medium distance vision, or reading vision, for example. The control module may be pre-calibrated to convert these pre-selected user inputs to instructions. The pump may switch between a plurality of pre-calibrated settings. Each setting may correspond to a distance.

Whilst the present disclosure has been described and illustrated with reference to particular embodiments, it will be appreciated by those of ordinary skill in the art that the present disclosure lends itself to many different variations not specifically illustrated herein. By way of example only, certain possible variations will now be described.

Optionally, the pump is an actuator.

Optionally, the osmotic pump may be in direct fluid communication with the annular ring. In such embodiments, the osmotic fluid that is induced to pass through the osmotic membrane is the same fluid that is used to fill the annular ring. Therefore, when the annular ring is desired to be inflated, fluid from the fluid reservoir will be induced to pass through the osmotic membrane and into the annular ring. In alternative embodiments of the present disclosure, the osmotic pump may not be in direct fluid communication with the annular ring. In such embodiments, the osmotic fluid that is induced to pass through the osmotic membrane fills up a separate, impermeable, zone. The increase in volume of the separate zone forces fluid to flow from the reservoir into the annular ring.

In some example embodiments of the present disclosure, the fluid that fills the central region is saline. The fluid that fills the central region may be water based. Alternatively, the fluid that fills the central region may be oil based. In embodiments of the present disclosure, the fluid that fills the central region may be a mixture of oil based, and water based, fluids.

Optionally, the central region is an oval in plan view. The annular ring may also be an oval ring, such that the internal circumference of the annular ring is in contact with the circumferential wall of the central region.

Optionally, the method of manufacture may comprise providing a hydrophobic coating. The hydrophobic coating may be provided on at least part of the concave surface of the second lens portion. The hydrophobic coating may alternatively or additionally be provided on at least part of the convex surface of the first lens portion. The parts of the first and/or second lens portions that are coated with hydrophobic coating may be arranged to form the central region and/or the inflatable ring.

Advantageously, the use of a hydrophobic coating in the regions of the lens where liquid is stored improves the retention of liquid within the lens. Soft contact lenses may transmit water to help to ensure that they do not stick to the eye. The hydrophobic coating can ensure that the liquid contained within the lens does not leave its confinement.

The skilled person will appreciate that the first lens portion may optionally be formed of an alternative material to silicone elastomer. The first lens portion may be made of any other suitable first lens portion material, such as hydrogel, or rigid gas permeable lenses made from silicone acrylate or variants of such.

The invention claimed is:

1. A tuneable contact lens comprising:
a central region having (i) a circumferential wall and (ii) an anterior surface having an external curvature;
an inflatable ring arranged around the circumferential wall of the central region;
a pump; and
at least one fluid reservoir in fluid connection with the inflatable ring, wherein
the pump is arranged to pump fluid from the at least one fluid reservoir to the inflatable ring, thereby inflating the inflatable ring and thereby changing the external curvature of the anterior surface of the central region, and thereby changing the optical power of the lens.

2. The tuneable contact lens as claimed in claim 1, wherein the inflatable ring shares in common with the central region the circumferential wall so that the thickness of the of the central region at its circumference increases as the inflatable ring inflates.

3. The tuneable contact lens as claimed in claim 1, wherein the pump includes a wireless communication module.

4. The tuneable contact lens as claimed in claim 3, wherein the wireless communication module is configured to communicate with a control unit, wherein the control unit is external to the contact lens.

5. The tuneable contact lens as claimed in claim 4, wherein the control unit transmits a setting to the pump, wherein the volume of fluid pumped by the pump is a function of the setting.

6. The tuneable contact lens as claimed in claim 1, wherein the pump is an osmotic pump or a mechanical pump or is an actuator.

7. The tuneable contact lens as claimed in claim 1, wherein in use the inflatable ring is arranged to contain at least a minimum volume of fluid.

8. The tuneable contact lens as claimed in claim 1, wherein the central region is circular.

9. The tuneable contact lens as claimed in claim 1, wherein the central region comprises a liquid filled zone.

10. The tuneable contact lens as claimed in claim 1, wherein the inflatable ring is a continuous ring, and wherein the inflatable ring continuously surrounds the circumferential wall of the central region.

11. The tuneable contact lens as claimed in claim 1, wherein the inflatable ring comprises at least three discrete inflatable portions, the at least three inflatable portions being arranged around the central region to form the ring, each of the at least three portions being positioned to be adjacent to a portion of the circumferential wall of the central region.

12. A method of manufacturing a contact lens according to claim 1, the method comprising the steps of:
    forming a first lens portion;
    forming a second lens portion;
    forming a first and a second recess and a fluid reservoir in the first and/or second lens portion;
    positioning a pump to be in fluid communication with the fluid reservoir; and
    bonding the second lens portion to the first lens portion, whereby the first recess forms a central region, and whereby the second recess forms an inflatable ring.

13. The method as claimed in claim 12, wherein the method further comprises the steps of:
    forming a first and second mold part;
    curing the first lens portion material between the first and second mold part.

14. The method as claimed in claim 12, wherein forming the second recess comprises plastically deforming the second lens portion.

15. A kit of parts comprising:
    (a) the tuneable contact lens as claimed in claim 1, the lens including a communication module; and
    (b) a control unit for communicating with the communication module.

16. The tuneable contact lens as claimed in claim 1, wherein the central region comprises a fixed volume.

17. The tuneable contact lens as claimed in claim 1, wherein the central region is a sealed region filled with fluid.

18. A method of tuning a tuneable contact lens, the contact lens comprising: a central region having (i) a circumferential wall and (ii) an anterior surface having an external curvature; an inflatable ring arranged around the circumferential wall of the central region; a fluid reservoir in fluid connection with the inflatable ring; and a pump wherein the pump is arranged to pump fluid from the fluid reservoir to the inflatable ring, the method comprising the steps of:
    activating the pump to pump fluid from the fluid reservoir to the inflatable ring;
thereby inflating the inflatable ring and thereby changing the external curvature of the anterior surface, and thereby changing the optical power of the lens.

\* \* \* \* \*